United States Patent [19]

Michna et al.

[11] Patent Number: 4,548,761
[45] Date of Patent: Oct. 22, 1985

[54] PROCESS FOR THE PREPARATION OF 1-AMINOBENZENE-2-SULPHONIC ACIDS

[75] Inventors: Martin Michna; Hermann Henk, both of Cologne, Fed. Rep. of Germany

[73] Assignee: Bayer Aktiengesellschaft, Leverkusen, Fed. Rep. of Germany

[21] Appl. No.: 502,077

[22] Filed: Jun. 8, 1983

[30] Foreign Application Priority Data

Jun. 29, 1982 [DE] Fed. Rep. of Germany ....... 3224155

[51] Int. Cl.$^4$ .......................................... C07C 143/58
[52] U.S. Cl. ................................... 260/508; 260/509; 260/510; 260/465 E; 568/25; 568/67; 548/260
[58] Field of Search .......... 260/508, 509, 510, 465 E; 568/25, 67; 548/260

[56] References Cited

U.S. PATENT DOCUMENTS 2,642,458  6/1953  Erickson ......................... 260/507 R
3,038,932  6/1962  Hardy et al. ........................ 260/508
3,329,708  7/1967  Berger ............................. 260/513 R
3,670,002  6/1972  Sheng et al. .................... 260/453 R

FOREIGN PATENT DOCUMENTS 0025274  3/1981  European Pat. Off. .

Primary Examiner—Nicky Chan
Attorney, Agent, or Firm—Sprung, Horn, Kramer & Woods

[57] ABSTRACT

Process for the preparation of 1-aminobenzene-2-sulphonic acids of the formula

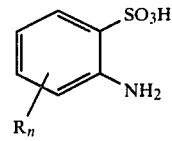

wherein
R=H or a substituent and
n=1-4, and their salts, in particular their alkali metal salts, by oxidation of compounds of the formula

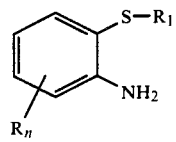

wherein
$R_1$=H, a cation, in particular an alkali metal cation, or a radical of the formula

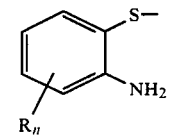

characterized in that the oxidation is carried out in a weakly acidic to alkaline pH range. The process can also be carried out as a one-pot process, using the corresponding benzothiazoles as starting materials.

6 Claims, No Drawings

PROCESS FOR THE PREPARATION OF 1-AMINOBENZENE-2-SULPHONIC ACIDS

The present invention relates to a process for the preparation of 1-aminobenzene-2-sulphonic acids of the formula

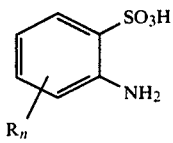

wherein
R=H or a substituent and
n=1-4,
and their salts, in particular the alkali metal salts, by oxidation of compounds of the formula

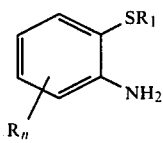

wherein
$R_1$=H, a cation, in particular an alkali metal cation, or a radical of the formula

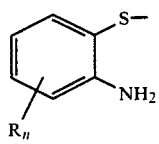

characterised in that the oxidation is carried out in the weakly acidic to alkaline pH range, preferably at pH values of about 5-14, in particular about 8-14.

The compounds II are obtained, for example, by alkaline hydrolysis of benzothiazoles of the formula

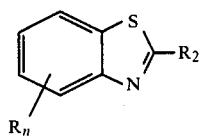

wherein
$R_2$=H or a substituent and
R and n have the meaning given above.

The oxidation is preferably carried out in an aqueous medium which can, if required, contain organic, water-miscible solvents which are stable to oxidising agents under the reaction conditions.

The oxidation is carried out at temperatures of about 20° to 100° C., in particular about 50° to 100° C. Examples of suitable oxidising agents are: oxygen, halogens, such as chlorine or bromine, permanganates, chromates, nitrates, iron(III) salts and preferably peroxides, in particular hydrogen peroxide, and other per compounds, such as perborates, persulphates, percarbonates, percarboxylic acids and persulphonic acids. If appropriate, suitable catalysts can also be added, for example tungstates, vanadates, molybdates and iron(II) salts.

The oxidising agents are employed in amounts of about 1-6 mols per mol of II.

The substituents R can be identical or different. Examples of suitable substituents are alkyl, in particular optionally substituted $C_1$-$C_4$-alkyl, aryl, in particular optionally substituted phenyl, nitro, sulpho, CN, halogen, in particular Cl, OH, SH, $NH_2$, alkoxy, in particular optionally substituted $C_1$-$C_4$-alkoxy, arylazo, in particular optionally substituted phenylazo, and naphthotriazol-2-yl or benzotriazol-2-yl which is optionally further substituted.

Suitable substituents $R_2$ are, in particular, $NH_2$, OH, Cl, $SO_3H$, SH and alkyl, in particular optionally substituted $C_1$-$C_4$-alkyl.

Examples of suitable starting compounds III are benzothiazole, mercaptobenzothiazole, 2-methyl-6-nitrobenzothiazole, 2-amino-6-methoxy-benzothiazole, 2-chlorobenzothiazole and 6-sulphobenzothiazole.

A preferred embodiment of the process according to the invention is as follows: the compounds III are subjected to alkaline hydrolysis, preferably at pH values of about 10 to 14, this being carried out in an aqueous or aqueous-organic medium, and the product, without intermediate isolation, is then oxidised in a weakly acidic to alkaline range, in particular at pH values of about 5 to 14, preferably about 8-14, preferably with hydrogen peroxide.

The reaction can also be carried out in such a manner that the hydrolysis is effected at the same time as the oxidation to I. In a further process variant, it is also possible first to hydrolyse III, then to oxidise the product with oxidising agents under mild conditions to give the disulphide, and thereafter to oxidise this under relatively severe conditions to give I.

The compounds I are known. They are employed, for example, as diazo components for the preparation of azo dyestuffs. The preparation of I from II by oxidation in a strongly acidic medium had already been disclosed in U.S. patent specification No. 3,038,932.

Surprisingly, the oxidation can also be carried out in a weakly acidic or alkaline medium without byproducts occurring; instead, purer products are obtained than in the case of oxidation in a strongly acidic medium.

EXAMPLE 1

35 g of mercaptobenzothiazole are boiled under reflux with 50 g of NaOH and 400 ml of water for 3 to 5 hours. The solution obtained is allowed to cool to 50° C., and 30% strength hydrogen peroxide is slowly added dropwise until the oxidising agent is no longer consumed. The mixture is heated further for a short time to 80°-90° C., approx. 10 g of active charcoal and a small amount of a filtration aid are added, and insoluble residues are filtered off. The solution is then allowed to cool, the o-sulphanilic acid formed is precipitated by acidification to pH 1, and the precipitate is filtered off under suction and dried.

Yield: approx. 30-31 g.

EXAMPLE 2

1 mol of 2-methyl-6-nitro-benzothiazole in 1.2 liters of 3% strength NaOH is boiled until a solution is formed. This is allowed to cool to approx. 30° C., and 1 mol of hydrogen peroxide, in the form of a 35% strength aqueous solution, is added dropwise in the course of approx. 1 hour. The temperature should not exceed 50° C. Thereafter, a further 2 mols of 35% strength hydrogen peroxide are added dropwise in the course of 1 hour, the temperature increasing to the boiling point. The mixture is allowed to cool to 80° C., 10 g of active charcoal and 10 g of a customary filtration aid are added, the mixture is filtered, the filtrate is cooled to 5°–10° C., and the 2-amino-5-nitro-benzene-sulphonic acid formed is precipitated by the addition of concentrated hydrochloric acid.

Yield: approx. 80% of theory.

EXAMPLE 3

18 g of 2-amino-6-methoxy-benzothiazole are boiled with 300 ml of water and 15 g of NaOH until ammonia is no longer evolved. The solution obtained is brought to 50° C., and air is passed through until a chromatogram indicates that complete oxidation to 2,2'-diamino-5,5'-dimethoxydiphenyl disulphide has occurred. Thereafter, 18 ml of 35% strength hydrogen peroxide are added dropwise, the temperature increasing to 80°–100° C. 10 g of active charcoal and 5 g of kieselguhr are added, and the mixture is stirred for 30 minutes and clarified. The resulting solution of the sodium salt of 2-amino-5-methoxybenzenesulphonic acid can be directly processed further.

EXAMPLE 4

1 mol of benzothiazole is boiled under reflux with 200 ml of water and 220 ml of 40% strength sodium hydroxide solution for 5 hours, while stirring vigorously. The solution is cooled to 20°–30° C. First, 86 ml of 35% strength hydrogen peroxide are added slowly to the cooled solution. During the addition, the temperature should not exceed 50° C. Thereafter, a further 152 ml of 35% strength hydrogen peroxide are added dropwise in the course of one hour. The temperature increases to 95° C. during the addition, and the initially precipitated 2,2'-diaminodiphenyl disulphide is converted to 2-aminobenzenesulphonate. After the addition of hydrogen peroxide is complete, the mixture is kept at 95° C. for a further 30 minutes. It is allowed to cool to 80° C., 5 g of active charcoal and 10 g of customary filtration aid are added, and the solution is clarified. The clarified solution is cooled to 5°–10° C. and acidified to pH 0.5–1, and the precipitated o-sulphanilic acid is filtered off under suction. Yield: 122 g (70%). The mother liquor contains a further 30 g of o-sulphanilic acid.

We claim:

1. Process for the preparation of 1-aminobenzene-2-sulphonic acid of the formula

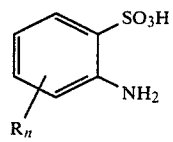

wherein
R=H, $C_1$-$C_4$-alkyl, $C_1$-$C_4$-alkoxy, phenyl, nitro, sulfo, CN, Cl, OH, SH, $NH_2$, naphthotriazolyl-2- or benzotriazolyl-2- and
n=1–4,
and a salt thereof, by oxidation of a compound of the formula

wherein
$R_1$=H, a cation, or a radical of the formula

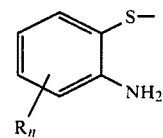

characterised in that the oxidation is carried out in a pH range of 8–14.

2. Process according to claim 1, characterised in that oxidation is effected at pH values of 10–14.

3. Process according to claim 2, characterised in that oxidation is effected in an aqueous medium.

4. Process according to claim 3, characterised in that oxidation is effected at temperatures of about 50°–100° C.

5. Process according to claim 1, characterised in that oxidation is effected with hydrogen peroxide.

6. Process for the preparation of the 1-aminobenzenesulphonic acid of claim 1, characterised in that benzothiazole of the formula

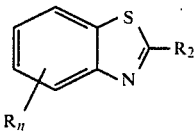

wherein
R and n have the meaning given in claim 1 and
$R_2$ represents H, OH, Cl or SH is hydrolysed in an aqueous or aqueous-organic medium, and the resulting reaction product, without intermediate isolation, is oxidised in a pH range 8–14.

* * * * *